United States Patent

Denomme et al.

Patent Number: 5,099,682
Date of Patent: Mar. 31, 1992

[54] MEAT DONENESS TESTER

[76] Inventors: Catherine E. Denomme; Viggo Lundhild, Sr., both of 79 High Falls, Wawa, Ontario, Canada, P0S 1K0

[21] Appl. No.: 491,827

[22] Filed: Mar. 12, 1990

[51] Int. Cl.$^5$ .................. G01N 3/40; G01N 33/12
[52] U.S. Cl. .................................. 73/81; 73/866
[58] Field of Search ................ 73/78, 79, 81, 82, 83, 73/85, 866

[56] References Cited

U.S. PATENT DOCUMENTS

| | | | |
|---|---|---|---|
| 2,446,956 | 8/1948 | Ross | 73/81 |
| 2,652,718 | 9/1953 | Wiseman | 73/78 |
| 3,554,018 | 1/1971 | Anderson et al. | 73/81 |
| 3,602,038 | 8/1971 | Hansen | 73/81 |
| 3,839,908 | 10/1974 | Casper | 73/862.47 |
| 4,141,239 | 2/1979 | Gilbert | 73/81 |
| 4,939,927 | 7/1990 | Johnston | 73/81 |

FOREIGN PATENT DOCUMENTS

| | | | |
|---|---|---|---|
| 58399 | 10/1967 | Fed. Rep. of Germany | 73/81 |
| 2638261 | 3/1977 | Fed. Rep. of Germany | 73/81 |
| 1179835 | 5/1959 | France | 73/81 |
| 593112 | 2/1978 | U.S.S.R. | 73/81 |
| 2146129 | 4/1985 | United Kingdom | 73/81 |

Primary Examiner—Tom Noland
Attorney, Agent, or Firm—R. Craig Armstrong

[57] ABSTRACT

A meat doneness tester is disclosed. The invention uses the known principle that the doneness of the meat is directly proportional to the firmness of the meat, i.e. the more the meat is cooked the firmer it becomes. The invention includes a body member, the lowermost portion(s) of the body member being co-planar, with the plane constituting a reference plane for positioning against the surface of the meat. A probe is attached to the body member for up and down movement towards and away from the body member beneath the body member. The probe is biased downwardly by a spring member, i.e. away from said body member. An indicator member is provided for indicating the displacement of the probe member from the reference plane. In the preferred embodiment, the probe, the spring member and the indicator member are provided in the form of a single element, namely a spring steel strip. The strip is fastened to the body, and a probe portion is produced by forming the strip into a downwardly-projecting V-shape. The free end of the strip constitutes an indicator, which points to a scale inscribed on the body member.

5 Claims, 2 Drawing Sheets

MEAT DONENESS TESTER

BACKGROUND OF THE INVENTION

This invention relates to devices for testing the doneness of meat.

It is an object of the invention to provide an improved means for testing the doneness of meat. Cookbooks provide charts that give cooking times for desired doneness based on the thickness of the piece of meat. This method is not very accurate because cooking times are affected by many other factors such as the temperature and shape of the meat. Most amateur cooks have to cut into the meat in order to be sure of its doneness. This defaces the meat and allows valuable juices to escape.

Various devices for testing the doneness of meat are known in the prior art. Examples of such devices are described and illustrated in U.S. Pat. No. 4,141,239 granted to Gilbert for a "Device and Kit and Method for Measuring the Degree of Doneness of a Cooked Piece of Meat" and U.S. Pat. No. 2,446,956 granted to Ross for a "Meat Testing Fork".

SUMMARY OF THE INVENTION

It is an object of the present invention to provide an improved meat tester.

In accordance with the present invention there is provided a meat tester that tests the doneness of a cooking piece of meat. The meat tester works equally well on steaks and hamburgers and is just as effective when frying, broiling, baking or barbecuing. The invention uses the known principle that the doneness of the meat is directly proportional to the firmness of the meat, i.e. the more the meat is cooked the firmer it becomes.

The invention includes a body member, the lowermost portion(s) of the body member being co-planar, with the plane constituting a reference plane for positioning against the surface of the meat. A probe is attached to the body member for up and down movement towards and away from the body member beneath the body member. Spring means bias the probe downwardly, i.e. away from said body member. Indicator means are provided for indicating the displacement of the probe member from the reference plane.

Further features of the invention will be described or will become apparent in the course of the following detailed description.

BRIEF DESCRIPTION OF THE DRAWINGS

In order that the invention may be more clearly understood, the preferred embodiment thereof will now be described in detail by way of example, with reference to the accompanying drawings, in which.

DETAILED DESCRIPTION OF THE PREFERRED EMBODIMENT

Figure 1:
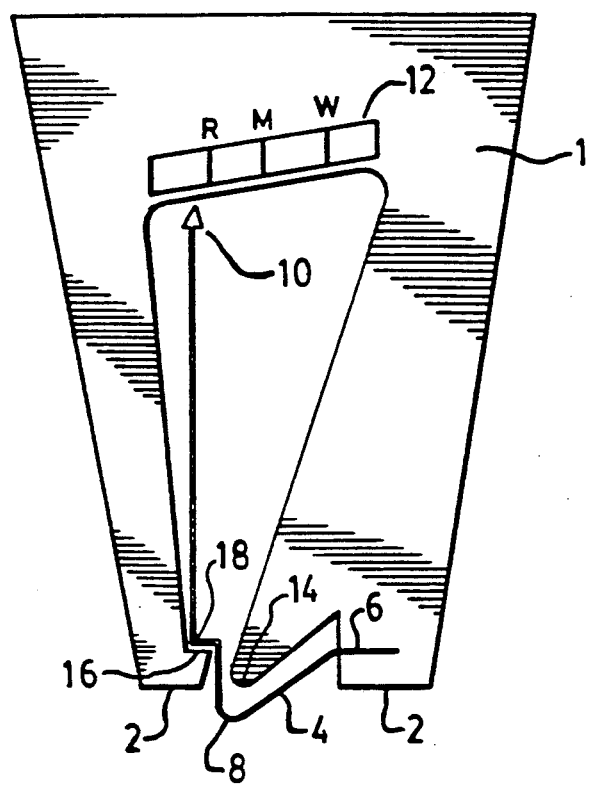
FIG. 1 is a side view of one embodiment of the invention.
Figure 2:
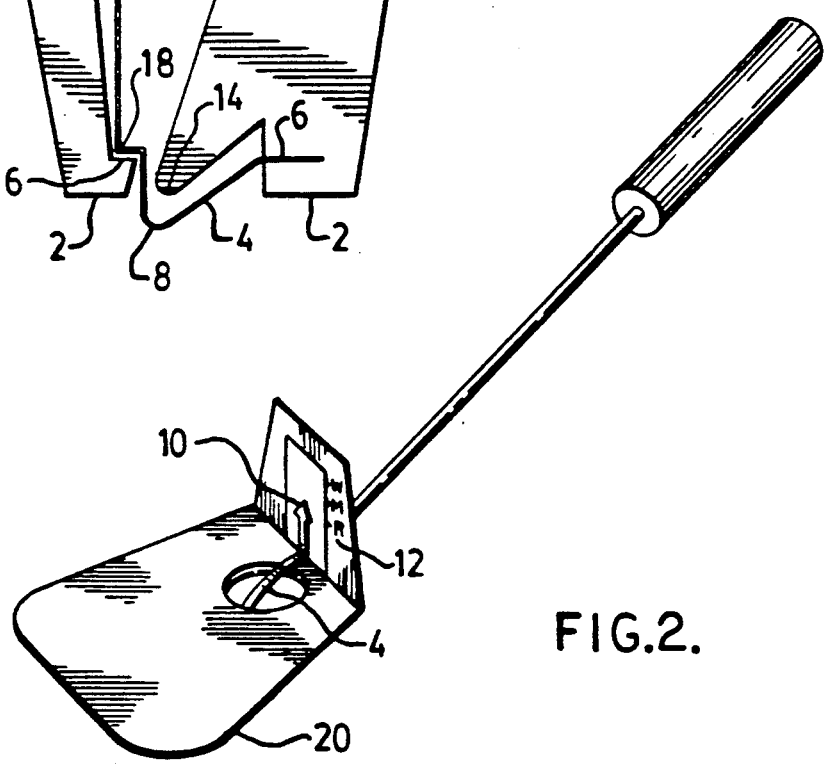
FIG. 2 is a perspective of an alternative embodiment of the invention, incorporated into a spatula.
Figure 3:
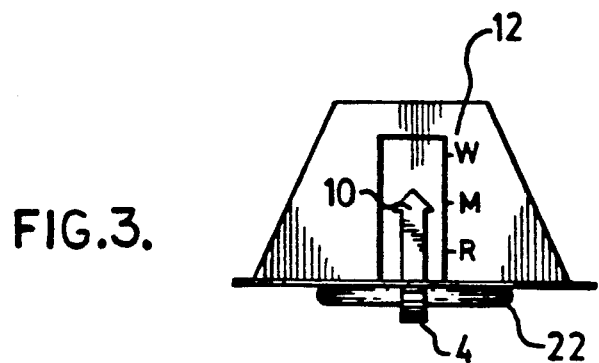
FIG. 3 is a rear view of the spatula.
Figure 4:
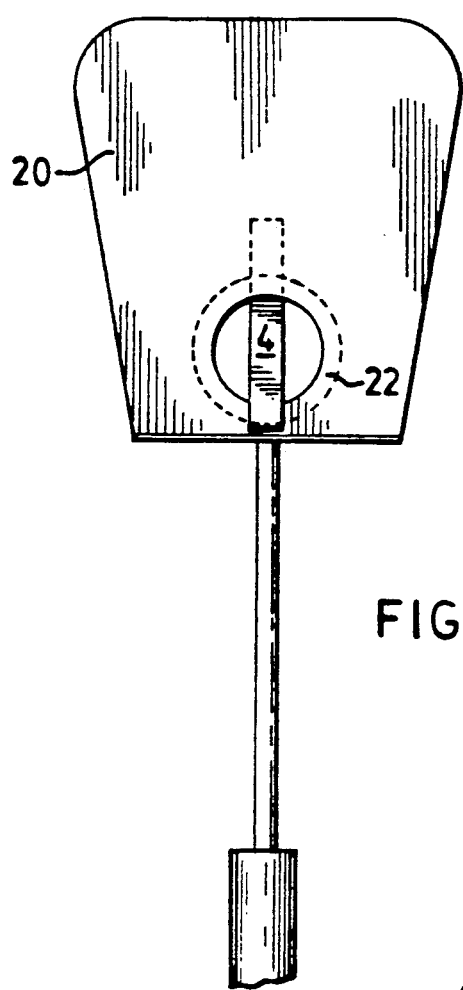
FIG. 4 is a top view of the spatula.
Figure 5:
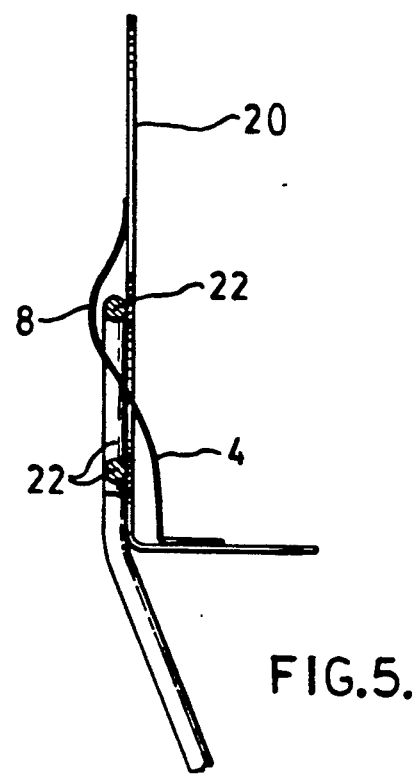
FIG. 5 is a side view of the spatula.

Referring to FIG. 1, the invention includes a body member or handgrip 1. The lowermost portions of the body member, i.e. the feet 2, are co-planar, with the plane constituting a reference plane for positioning against the surface of the meat. A probe, spring means and indicator means are provided in the form of a single element, namely the spring steel strip 4. The strip is fastened to the body in a slot 6, and a probe portion 8 is produced by forming the strip into a downwardly-projecting V-shape. The free end of the strip constitutes an indicator 10, which points to a scale 12 inscribed on the body member. This is the preferred arrangement, though it will be appreciated that the probe, spring means and indicator means could be separate elements, appropriately connected to each other. For example, there could be a probe which moved up and down in a channel, biased downwardly by a small coiled spring. The probe could act against a lever or other means which would provide an indication of the position of the probe.

To guard against inadvertent or intentional damage to the strip, excessive displacement into the body member is prevented by a spring guard 14. Excessive displacement away from the body member is prevented by a stop 16, a bend 18 being formed in the strip to act against the stop.

As can be readily appreciated from an examination of FIG. 1, the more firm the meat is, the closer to the body the probe portion 8 will be forced. This causes an appropriate deflection of the indicator 10. It is a relatively simple matter to calibrate the scale 12 so that it provides an accurate indication of the doneness of the meat, corresponding to the position of the probe and hence the deflection of the indicator.

It is an advantage of the preferred embodiment that a relatively small deflection of the probe is mechanically amplified to produce a larger deflection of the indicator, thus making the deflection easier to detect and the tester easier to read.

FIGS. 2 through 5 show an alternative embodiment, in which the invention is incorporated into a spatula 20. The principle is identical to the FIG. 1 embodiment. In this case the ring 22 acts in place of the spring guard 14 of FIG. 1. The upper surface of the spatula acts in place of the stop 16 of FIG. 1.

Figure 6:
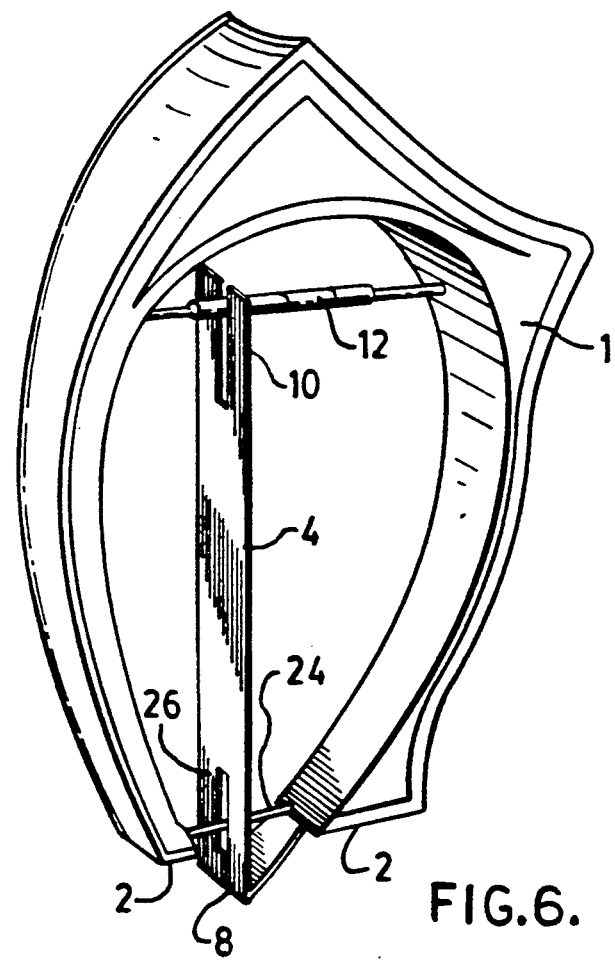
FIG. 6 is a perspective showing an alternative configuration.

FIG. 6 shows an alternative configuration, operating on the identical principle. In this case a rod 24 passing through a slot 26 in the strip 4 acts as the stop to limit movement of the strip.

It will be appreciated that the above description relates to the preferred embodiment by way of example only. Many variations on the invention will be obvious to those knowledgeable in the field, and such obvious variations are within the scope of the invention as described and claimed, whether or not expressly described.

For example, as has been mentioned above, the probe, spring means and indicator means could be separate elements, appropriately connected to each other.

In the preferred embodiment, it will be appreciated that the strip need not necessarily be of spring steel. Any other suitable resilient material could be used, including suitable metals or plastics. The exact configurations shown in the drawings could of course also be varied, without departing from the spirit and substance of the invention.

What is claimed as the invention is:

1. A meat doneness tester, comprising:

a body member having a substantially planar lower surface and an aperture through said lower surface;

a strip of spring metal having an end portion secured to said body member, an immediately adjacent probe portion projecting downwardly to slightly below the level of said lower surface of said body an thence upwardly through said aperture, and an elongated pointer portion leading from said probe portion, a small movement of said probe portion producing a substantially larger deflection of said pointer by virtue of said probe portion being adjacent said secure end and said pointer portion being elongated; and a scale on said body member adjacent said pointer portion for indicating the degree of deflection of said pointer portion.

2. A meat doneness tester as recited in claim 1, in which said body member has a cavity communicating with said aperture, said pointer portion being accommodated within said cavity.

3. A meat doneness tester as recited in claim 2, in which said body has at least one stop portion for engaging said spring metal strip to block movement of said probe substantially above the plane of said lower surface or below a normal resting level.

4. A meat doneness tester as recited in claim 1, in which said body has at least one stop portion for engaging said spring metal strip to block movement of said probe substantially above the plane of said lower surface or below a normal resting level.

5. A meat doneness tester as recited in claim 1, in which said body comprises a spatula blade, said spatula blade having an upwardly projecting portion bearing said scale.

* * * * *